(12) United States Patent
Ishiai

(10) Patent No.: US 10,314,480 B2
(45) Date of Patent: Jun. 11, 2019

(54) OPHTHALMOLOGIC IMAGING APPARATUS AND METHOD FOR CONTROLLING THE SAME

(71) Applicant: KABUSHIKI KAISHA TOPCON, Itabashi-ku (JP)

(72) Inventor: Ryota Ishiai, Kita-ku (JP)

(73) Assignee: KABUSHIKI KAISHA TOPCON, Itabashi-ku (JP)

( * ) Notice: Subject to any disclaimer, the term of this patent is extended or adjusted under 35 U.S.C. 154(b) by 46 days.

(21) Appl. No.: 15/500,665

(22) PCT Filed: Jul. 13, 2015

(86) PCT No.: PCT/JP2015/070006
§ 371 (c)(1),
(2) Date: Jan. 31, 2017

(87) PCT Pub. No.: WO2016/027589
PCT Pub. Date: Feb. 25, 2016

(65) Prior Publication Data
US 2017/0215725 A1    Aug. 3, 2017

(30) Foreign Application Priority Data
Aug. 19, 2014  (JP) .................. 2014-166522

(51) Int. Cl.
*A61B 3/10* (2006.01)
*A61B 3/00* (2006.01)
(Continued)

(52) U.S. Cl.
CPC ............ *A61B 3/102* (2013.01); *A61B 3/0025* (2013.01); *A61B 3/0041* (2013.01);
(Continued)

(58) Field of Classification Search
CPC ......... A61B 3/102; A61B 3/14; A61B 3/0041; A61B 3/12; A61B 3/1225; A61B 3/0025
See application file for complete search history.

(56) References Cited

U.S. PATENT DOCUMENTS

2011/0286003 A1  11/2011  Ono
2012/0140179 A1   6/2012  Miyasa et al.
(Continued)

FOREIGN PATENT DOCUMENTS

JP    2010-181172 A    8/2010
JP    2011-36431 A     2/2011
(Continued)

OTHER PUBLICATIONS

International Search Report dated Oct. 13, 2015 in PCT/JP2015/070006 filed Jul. 13, 2015.
(Continued)

*Primary Examiner* — Jack Dinh
(74) *Attorney, Agent, or Firm* — XSENSUS LLP

(57) ABSTRACT

An ophthalmologic imaging apparatus includes a data acquisition unit and a controller. The data acquisition unit is configured to repeatedly acquire data by repeatedly scanning an eye using optical coherence tomography. The controller is configured to perform first control to adjust optical path length difference between a sample arm and a reference arm of an interference optical system for optical coherence tomography to place an image of the eye in a reference position in an image frame based on the data repeatedly acquired by the data acquisition unit. Further, the controller is configured to perform second control to change the optical path length difference so as to place the image of the eye in a new reference position in the image frame based on the data repeatedly acquired by the data acquisition unit. The
(Continued)

apparatus can perform preparatory operations for OCT measurement of the subject's eye.

14 Claims, 7 Drawing Sheets

(51) Int. Cl.
*A61B 3/12* (2006.01)
*A61B 3/14* (2006.01)
*A61B 3/15* (2006.01)

(52) U.S. Cl.
CPC .............. *A61B 3/0075* (2013.01); *A61B 3/12* (2013.01); *A61B 3/1225* (2013.01); *A61B 3/14* (2013.01); *A61B 3/152* (2013.01)

(56) References Cited

U.S. PATENT DOCUMENTS

| | | |
|---|---|---|
| 2012/0281235 A1 | 11/2012 | Murata et al. |
| 2013/0242258 A1 | 9/2013 | Higuchi |
| 2013/0258349 A1 | 10/2013 | Makihira et al. |
| 2015/0335237 A1 | 11/2015 | Okada et al. |

FOREIGN PATENT DOCUMENTS

| | | |
|---|---|---|
| JP | 2011-92290 A | 5/2011 |
| JP | 2012-223264 A | 11/2012 |
| JP | 2013-188316 A | 9/2013 |
| JP | 2013-212173 A | 10/2013 |
| JP | 2014-113175 A | 6/2014 |
| JP | 2014-140542 A | 8/2014 |

OTHER PUBLICATIONS

Notification of Reasons for Refusal issued in Japanese Application 2014-166522 dated Apr. 2, 2019.

OPHTHALMOLOGIC IMAGING APPARATUS AND METHOD FOR CONTROLLING THE SAME

TECHNICAL FIELD

Embodiments described herein relate generally to an ophthalmologic imaging apparatus that acquires images of eyes using optical coherence tomography (OCT), and a method for controlling the same.

BACKGROUND ART

In recent years, OCT that uses interference of light to image a surface morphology and internal morphology of an object is attracting a lot of attention. OCT is noninvasive to human bodies unlike X-ray computed tomography (CT) system. Therefore, application of OCT to medical and biological fields is expected. For example, OCT systems for imaging an eye fundus, cornea, or the like have already been practicalized.

In general, an ophthalmologic imaging apparatus that uses OCT performs a variety of preparatory operations before performing OCT measurement. Examples of the preparatory operations include alignment, optical path length difference adjustment, polarization adjustment, and focus adjustment. In the alignment, registration (position adjustment) of an optical system of the apparatus to a subject's eye is performed. In the optical path length difference adjustment, the difference between the optical path length of measurement light and that of reference light is adjusted to render a target site of the subject's eye in a suitable area in an image frame. In the polarization adjustment, the polarization state of one or both of the measurement light and reference light is adjusted for improving the efficiency of interference between the measurement light and reference light. In the focus adjustment, focus of the measurement light is adjusted to position the beam waist of the measurement light to or near the target site.

PRIOR ART DOCUMENT

Patent Document

[Patent Document 1] Japanese Unexamined Patent Publication No. 2014-113175

SUMMARY OF THE INVENTION

Problems to be Solved by the Invention

In the ophthalmologic field, an object to be imaged is a living eye. The living eye is always moves due to body motion, eye movement, pulsation, and the like. Accordingly, the subject's eye moves during the preparatory operations and during the period from the completion of the preparatory operations to the commencement of OCT measurement. For example, when the subject's eye moves in the travelling direction of the measurement light (the depth direction of the subject's eye), a site of interest is rendered near the edge of the imaging range of the OCT measurement (near the edge of the image frame). Moreover, in some cases, the site of interest is located outside of the image frame. In those cases, problems arise in which the preparatory operations cannot be performed properly any more, or in which the image of the site of interest cannot be obtained.

The purpose of the invention is to properly perform the preparatory operations for OCT measurement of the subject's eye.

Means of Solving the Problems

According to one embodiment, an ophthalmologic imaging apparatus includes a data acquisition unit and a controller. The data acquisition unit is configured to repeatedly acquire data by repeatedly scanning an eye using optical coherence tomography. The controller is configured to perform first control to adjust optical path length difference between a sample arm and a reference arm of an interference optical system for optical coherence tomography so as to place an image of the eye in a reference position in an image frame based on the data repeatedly acquired by the data acquisition unit. Further, the controller is configured to perform second control to change the optical path length difference so as to place the image of the eye in a new reference position in the image frame based on the data repeatedly acquired by the data acquisition unit.

Effects of the Invention

According to one embodiment, preparatory operations for OCT measurement of the subject's eye can be properly performed.

MODES FOR CARRYING OUT THE INVENTION

Figure 1:
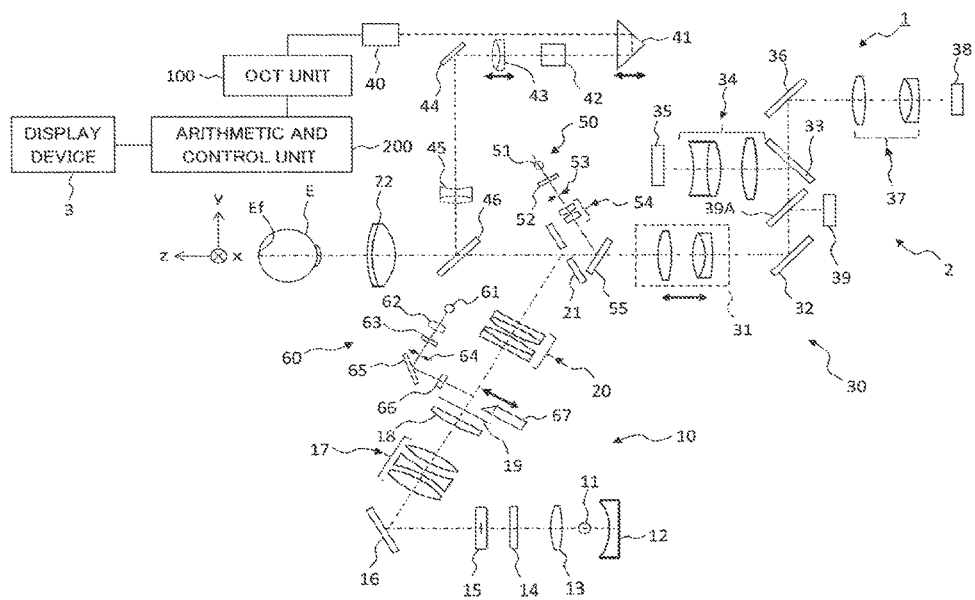
FIG. 1 is a schematic diagram illustrating an example of the configuration of an ophthalmologic imaging apparatus according to an embodiment.

Referring now to the drawings, a detailed description is given of illustrative embodiments of the present invention. An ophthalmologic imaging apparatus according to an embodiment forms tomographic images, three-dimensional images, etc. of eyes using OCT. In the specification, images acquired by using OCT may sometimes be referred to as "OCT images". In addition, measuring operations performed for obtaining OCT images may sometimes be referred to as "OCT measurement". Incidentally, the disclosure of the documents cited herein may be incorporated in the following embodiments.

The following embodiment describes an application of Fourier-domain OCT. In particular, as the apparatus disclosed in the Patent document 1, an ophthalmologic imaging apparatus described in the embodiment is configured to be able to acquire OCT images of an eye fundus by using spectral-domain OCT and acquire a fundus image. The configuration described in the embodiment may be applied to ophthalmologic imaging apparatuses using other types of OCT than spectral-domain OCT, such as swept-source OCT. Although the embodiment describes a multifunctional apparatus including an OCT device and a fundus camera, the configuration for OCT described in the embodiment may be combined with other types of ophthalmologic imaging apparatuses than the retinal camera, such as a scanning laser ophthalmoscope (SLO), a slit lamp microscope, an ophthalmic surgical microscope). Alternatively, the configuration of the embodiment may be applied to an (single-functional) OCT device.

In the following embodiments, a description is given of a case of eye fundus imaging: however, other sites of eyes may be imaged. For example, the configuration described in the embodiment may be applied to devices used for anterior segment OCT (e.g., for corneal OCT). Further, the configuration described in the embodiment may be applied to devices used for both fundus OCT and anterior segment OCT. As an example of this case, the configuration for fundus imaging described in the embodiment may be supplemented with an attachment for anterior segment imaging (e.g., objective lens, front lens).

[Configuration]

Figure 2:
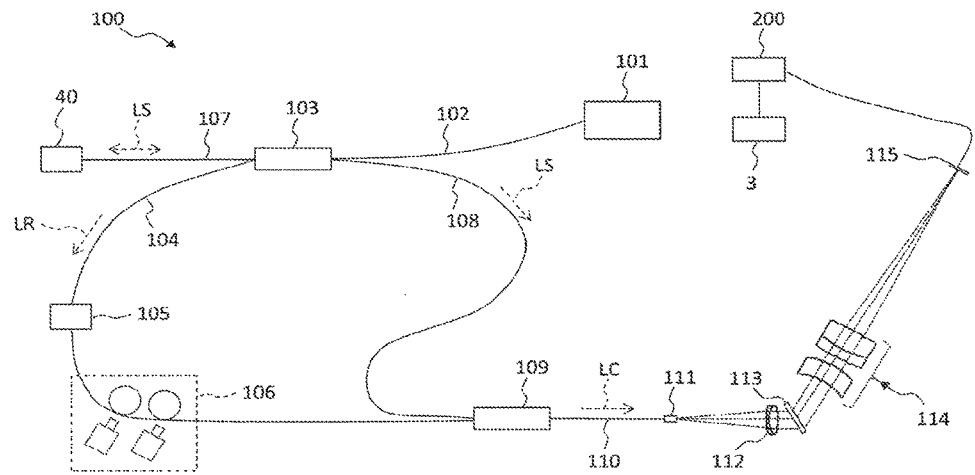
FIG. 2 is a schematic diagram illustrating an example of the configuration of the ophthalmologic imaging apparatus of the embodiment.

As illustrated in FIGS. 1 and 2, an ophthalmologic imaging apparatus 1 includes a fundus camera unit 2, an OCT unit 100, and an arithmetic and control unit 200. The fundus camera unit 2 is provided with an optical system for photographing a fundus to obtain front images of the fundus. The OCT unit 100 is provided with an optical system for obtaining OCT images of the fundus. The arithmetic and control unit 200 is provided with a computer for performing various arithmetic processes and control processes. A display device 3 displays various information. The display device 3 may be included in the ophthalmologic imaging apparatus 1, or may be provided outside of the ophthalmologic imaging apparatus 1.

[Fundus Camera Unit]

As illustrated in FIG. 1, the fundus camera unit 2 is provided with an optical system for acquiring two-dimensional images (fundus images) rendering the surface morphology of a fundus Ef of a subject's eye E. Examples of the fundus images include observation images and photographed images. An observation image is, for example, a monochrome moving image formed at a predetermined frame rate using near-infrared light. A photographed image is, for example, a color image captured by flashing visible light, or a monochrome still image using near-infrared light or visible light as illumination light. The fundus camera unit 2 may be configured to be capable of acquiring other types of images such as fluorescein angiograms, indocyanine green angiograms, and autofluorescent angiograms.

The fundus camera unit 2 is provided with a jaw holder and a forehead rest for supporting the face of the subject. Further, the fundus camera unit 2 is provided with an illumination optical system 10 and an imaging optical system 30. The illumination optical system 10 projects illumination light onto the fundus Ef. The imaging optical system 30 guides the illumination light reflected from the fundus Ef to imaging devices (CCD image sensors 35 and 38). Each of the CCD image sensors 35 and 38 is sometimes simply referred to as a "CCD". Further, the imaging optical system 30 guides measurement light (or, signal light, sample light, etc.) coming from the OCT unit 100 to the fundus Ef, and guides the measurement light returning from the fundus Ef to the OCT unit 100.

An observation light source 11 in the illumination optical system 10 includes, for example, a halogen lamp. Light emitted from the observation light source 11 (observation illumination light) is reflected by a reflection mirror 12 having a curved reflective surface, refracted by a condenser lens 13, and becomes near-infrared light after passing through a visible cut filter 14. Further, the observation illumination light is once converged near a flash light source 15, reflected by a mirror 16, and passes through relay lenses 17 and 18, a diaphragm 19, and a relay lens 20. Then, the observation illumination light is reflected on the peripheral part (the surrounding region of an aperture part) of an aperture mirror 21, penetrates a dichroic mirror 46, refracted by an objective lens 22, and illuminates the fundus Ef. Note that a light emitting diode (LED) may be used as the observation light source 11.

The observation illumination light reflected from the fundus Ef (fundus reflection light) is refracted by the objective lens 22, penetrates the dichroic mirror 46, passes through the aperture part formed in the center region of the aperture mirror 21, passes through a dichroic mirror 55, is refracted by a focusing lens 31, and is reflected by a mirror 32. Further, the fundus reflection light passes through a half mirror 33A, is reflected by a dichroic mirror 33, and is converged on the light receiving surface of the CCD image sensor 35 by a condenser lens 34. The CCD image sensor 35 detects the fundus reflection light at a predetermined frame rate, for example. An image (observation image) obtained based on the fundus reflection light detected by the CCD image sensor 35 is displayed on the display device 3. Note that when the focus of the imaging optical system 30 is matched with the anterior eye segment of the eye E, an observation image of the anterior segment of the eye E is displayed.

The flash light source 15 includes, for example, a xenon lamp. Light emitted from the flash light source 15 (imaging illumination light) is projected onto the fundus Ef via the same route as that of the observation illumination light. Fundus reflection light of the imaging illumination light is guided to the dichroic mirror 33 via the same route as that of the observation illumination light, passes through the dichroic mirror 33, is reflected by a mirror 36, and is converged on the light receiving surface of the CCD image sensor 38 by a condenser lens 37. The display device 3 displays an image (photographed image) obtained based on the fundus reflection light detected by the CCD image sensor 38. Note that the same device or different devices may be used as the display device 3 for displaying the observation image and the display device 3 for displaying the photographed image. Besides, when similar photography is performed by illuminating the eye E with infrared light, an infrared photographed image is displayed. Note that an LED may be used as the flash light source 15.

The illumination optical system 10 includes a small-pupil diaphragm (microcoria diaphragm) that is inserted into the optical path. The small-pupil diaphragm is inserted in the optical path when the pupil of the eye E is small. The small-pupil diaphragm may be a diaphragm 19, for example. Note that when the pupil diameter of the eye E is normal, a diaphragm applied to photography of the eye E of normal pupil diameter (normal-pupil diaphragm) is inserted into the optical path as the diaphragm 19. Therefore, the diaphragm 19 includes the small-pupil diaphragm and the normal-pupil diaphragm which are selectively inserted into the optical path.

A liquid crystal display (LCD) 39 displays fixation targets, visual targets for visual acuity tests, etc. A fixation target is an indicator for fixating the eye E in a predetermined direction, and is used for fundus photography and OCT measurement.

Part of light emitted from the LCD 39 is reflected by the half mirror 33A, is reflected by the mirror 32, travels through the focusing lens 31 and the dichroic mirror 55, passes through the aperture part of the aperture mirror 21, penetrates the dichroic mirror 46, is refracted by the objective lens 22, and is projected onto the fundus Ef.

By changing the position of the fixation target displayed on the screen of the LCD 39, direction toward which the eye E is to be fixated (fixation position) can be changed. Examples of the fixation position include, as with conventional fundus cameras, a position for acquiring images centered on the macula of the fundus Ef, a position for acquiring images centered on the optic nerve head, a position for acquiring images centered on the fundus center between the macula and the optic nerve head. Further, the display position of the fixation target may be changed to any desired position.

Further, as with conventional fundus cameras, the fundus camera unit 2 is provided with an alignment optical system 50 and a focus optical system 60. The alignment optical system 50 generates an indicator (alignment indicator) for the registration of the optical system (alignment) with respect to the eye E. The focus optical system 60 generates an indicator (split indicator) for adjusting the focus position of the imaging optical system 30 with respect to the fundus Ef.

Light (alignment light) emitted from an LED 51 in the alignment optical system 50 travels through diaphragms 52 and 53 and a relay lens 54, is reflected by the dichroic mirror 55, passes through the aperture part of the aperture mirror 21, penetrates the dichroic mirror 46, and is projected onto the cornea of the eye E through the objective lens 22.

The alignment light reflected by the cornea (cornea reflection light) travels through the objective lens 22, the dichroic mirror 46 and the aperture part. Part of the cornea reflection light then penetrates the dichroic mirror 55, passes through the focusing lens 31, is reflected by the mirror 32, penetrates the half mirror 39A, is reflected by the dichroic mirror 33, and is projected onto the light receiving surface of the CCD image sensor 35 through the condenser lens 34. The display device 3 displays images (alignment indicator) captured by the CCD image sensor 35 together with the observation image. A user can conduct manual alignment operation while observing the alignment indicator. Although detail will be described later, alignment may be performed in such a way that the arithmetic and control unit 200 analyzes the position of the alignment indicator and moves the optical system (automatic alignment).

To conduct focus adjustment, the reflective surface of a reflection rod 67 is placed in a slanted position on the optical path of the illumination optical system 10. Light (focus light) emitted from an LED 61 in the focus optical system 60 passes through a relay lens 62, is split into two light beams by a split indicator plate 63, passes through a two-hole diaphragm 64, is reflected by a mirror 65, is converged on the reflective surface of the reflection rod 67 by a condenser lens 66, and is reflected by the reflection rod 67. Further, the focus light travels through the relay lens 20, is reflected by the aperture mirror 21, penetrates the dichroic mirror 46, is refracted by the objective lens 22, and is projected onto the fundus Ef.

The focus light reflected from the fundus passes through the same route as the cornea reflection light of the alignment light, and is detected by the CCD image sensor 35. The display device 3 displays images (split indicator) captured by the CCD image sensor 35 together with the observation image. As in the conventional fundus cameras, the user can perform manual focus adjustment operation while observing the split indicator. Although detail will be described later, focus adjustment may be performed in such a way that the arithmetic and control unit 200 analyzes the position of the split indicator and moves the focusing lens 31 and the focus optical system 60 (automatic focusing).

The dichroic mirror 46 branches the optical path for OCT measurement from the optical path for fundus photography. The dichroic mirror 46 reflects light of wavelengths used for OCT measurement, and transmits light for fundus photography. The optical path for OCT measurement is formed by, in order from the OCT unit 100 side, a collimator lens unit 40, an optical path length changing unit 41, a galvanometer scanner 42, a focusing lens 43, a mirror 44, and a relay lens 45.

The optical path length changing unit 41 is movable in the direction indicated by the arrow shown in FIG. 1 to change the length of the optical path for OCT measurement (sample arm). By changing the optical path length of the sample arm, the difference between the optical path length of the sample arm and the optical path length of the reference arm is changed. The difference between the optical path length of the sample arm and the optical path length of the reference arm is sometimes referred to as "optical path length difference". The change in the optical path length difference is used to correct the optical path length according to the axial length of the eye E, to adjust the interference state, or the like. The optical path length changing unit 41 includes, for example, a corner cube and a mechanism for moving the corner cube.

Other configurations may be employed to change the optical path length difference between the sample arm and the reference arm. For example, a configuration may be employed in which the reference arm includes a reflection mirror (reference mirror) in such a way that the reference mirror is moved in the travelling direction of the reference light. With this configuration, the optical path length difference is changed by changing the optical path length of the reference arm. Alternatively, the optical path length of the sample arm may be changed by moving the optical system for OCT measurement with respect to the eye E. In general, an optical path length difference changing unit has any configuration capable of changing at least one of the optical path length of the sample arm and the optical path length of the reference arm.

The galvanometer scanner 42 changes travelling direction of light (measurement light) travelling along the optical path for OCT measurement. Thereby, the fundus Ef can be scanned with the measurement light. The galvanometer scanner 42 includes, for example, a galvanometer mirror for x-directional scan, a galvanometer mirror for y-directional scan, and a mechanism for driving the galvanometer mirrors independently. Accordingly, the measurement light is deflected in any direction on the xy plane.

[OCT Unit]

A description is given of an example of the configuration of the OCT unit 100 with reference to FIG. 2. The OCT unit 100 is provided with an optical system for acquiring OCT images of the fundus Ef. The optical system is configured according to a conventional spectral-domain OCT. That is, the optical system is configured to: split low-coherence light into reference light and measurement light; make the measurement light returning from the fundus Ef and the reference light having travelled through the reference arm interfere with each other to generate interference light; and detect spectral components of the interference light. The detection result (detection signal) is sent to the arithmetic and control unit 200.

When swept-source OCT is employed instead of spectral-domain OCT, a wavelength tunable light source is provided instead of a low-coherence light source, and an optical member for spectrally decomposing interference light is not provided. Generally, the OCT unit 100 is configured through any known technology according to the type of OCT employed.

A light source unit 101 emits broadband, low-coherence light L0. The wavelength bands of the low-coherence light L0 includes, for example, near-infrared wavelengths (approximately 800 to 900 nm). The low-coherence light L0 has, for example, temporal coherence length of around several tens of micrometers. Note that, the low-coherence light L0 may be of wavelengths invisible for human eyes, such as near-infrared light with a central wavelength of around 1040 to 1060 nm.

The light source unit 101 includes a light emission device, such as a super luminescent diode (SLD), an LED, a semiconductor optical amplifier (SOA), or the like.

The low coherence light L0 emitted from the light source unit 101 is guided to a fiber coupler 103 through an optical fiber 102. The fiber coupler 103 splits the low coherence light L0 into measurement light LS and reference light LR.

The reference light LR is guided to an optical attenuator 105 through an optical fiber 104. The optical attenuator 105 automatically adjusts the amount of the reference light LR guided through the optical fiber 104 under the control of the arithmetic and control unit 200 using a known technology. The reference light LR with the light amount adjusted by the optical attenuator 105 is guided through the optical fiber 104 and arrives at a polarization adjuster (polarization controller) 106.

The polarization adjuster 106 applies external stress to the looped optical fiber 104 to adjust the polarization state of the reference light LR guided through the optical fiber 104. Note that the configuration of the polarization adjuster 106 is not so limited. Any known technology may be used for polarization adjustment. The reference light LR with polarization state adjusted by the polarization adjuster 106 arrives at a fiber coupler 109.

FIG. 2 describes a configuration in which the polarization state of the reference light LR is adjusted. However, a configuration may be employed in which the polarization state of the measurement light LS is adjusted. In general, at least one of the polarization state of the measurement light LS and the polarization state of the reference light LR may be adjusted. Thereby, it is possible to realize a control operation to match the polarization state of the measurement light LS and the polarization state of the reference light LR, which improves the efficiency of interference between the measurement light LS and the reference light LR.

The measurement light LS generated by the fiber coupler 103 is guided through an optical fiber 107 and collimated into a parallel light beam by the collimator lens unit 40. Further, the measurement light LS arrives at the dichroic mirror 46 via the optical path length changing unit 41, the galvanometer scanner 42, the focusing lens 43, the mirror 44, and the relay lens 45. Subsequently, the measurement light LS is reflected by the dichroic mirror 46, refracted by the objective lens 22, and projected onto the fundus Ef. The measurement light LS is scattered and reflected at various depth positions of the fundus Ef. Back-scattered light of the measurement light LS from the fundus Ef reversely advances along the same path as the outward path, and is guided to the fiber coupler 103. Then, the back-scattered light passes through an optical fiber 108, and arrives at the fiber coupler 109.

The fiber coupler 109 causes the back-scattered light of the measurement light LS and the reference light LR having passed through the optical fiber 104 to interfere with each other. Interference light LC thus generated is guided through an optical fiber 110, and output from an exit end 111. Further, the interference light LC is collimated into a parallel light beam by a collimator lens 112, spectrally decomposed (spectrally split and diffracted) by a diffraction grating 113, converged by a convergence lens 114, and projected onto the light receiving surface of a CCD image sensor 115. Note that FIG. 2 illustrates the diffraction grating 113 of the transmission type; however, a spectrally decomposing optical component of any other type, such as a diffraction grating of reflection type, may be used.

The CCD image sensor 115 is, for example, a line sensor. The CCD image sensor 115 detects the spectral components of the spectrally decomposed interference light LC, and converts the detected components into electric charges. The CCD image sensor 115 accumulates the electric charges to generate a detection signal, and sends the signal to the arithmetic and control unit 200.

Although a Michelson interferometer is used in the present embodiment, an interferometer of any type, such as Mach-Zehnder-type, may be used. In place of the CCD image sensor, an image sensor of other type, such as a complementary metal-oxide semiconductor (CMOS) image sensor, may be used. When swept-source OCT is employed, the diffraction grating 113 is not provided, and a balanced photodiode is provided in place of the CCD image sensor 115.

[Arithmetic and Control Unit]

Described blow is the configuration of the arithmetic and control unit 200. The arithmetic and control unit 200 analyzes detection signal s fed from the CCD image sensor 115 to form an OCT image of the fundus Ef. Arithmetic processes of the OCT image formation may be the same as those used in conventional spectral-domain OCT.

The arithmetic and control unit 200 controls each component of the fundus camera unit 2, the display device 3, and each component of the OCT unit 100.

For controlling the fundus camera unit 2, the arithmetic and control unit 200 controls the operation of the observation light source 11, the operation of the flash light source 15, the operations of the LEDs 51 and 61, the operation of the LCD 39, the movements of the focusing lenses 31 and 43, the movement of the reflection rod 67, the movement of the focus optical system 60, the movement of the optical path length changing unit 41, the operation of the galvanometer scanner 42, and the like.

For controlling the OCT unit 100, the arithmetic and control unit 200 controls the operation of the light source unit 101, the operation of the optical attenuator 105, the operation of the polarization adjuster 106, the operation of the CCD image sensor 115.

As in the conventional computer, the arithmetic and control unit 200 includes a microprocessor, RAM, ROM, hard disk drive, and communication interface, for example. Storage devices such as the hard disk drive store computer programs for controlling the ophthalmologic imaging apparatus 1. The arithmetic and control unit 200 may include various types of circuit boards, such as circuit boards for forming OCT images. Further, the arithmetic and control unit 200 may include operation devices (input devices) such as a keyboard and a mouse, and/or a display device such as an LCD.

The fundus camera unit 2, the display device 3, the OCT unit 100, and the arithmetic and control unit 200 may be integrally arranged (i.e., arranged in a single housing), or they may be separately provided in two or more housings.

[Control System]

Figure 3:
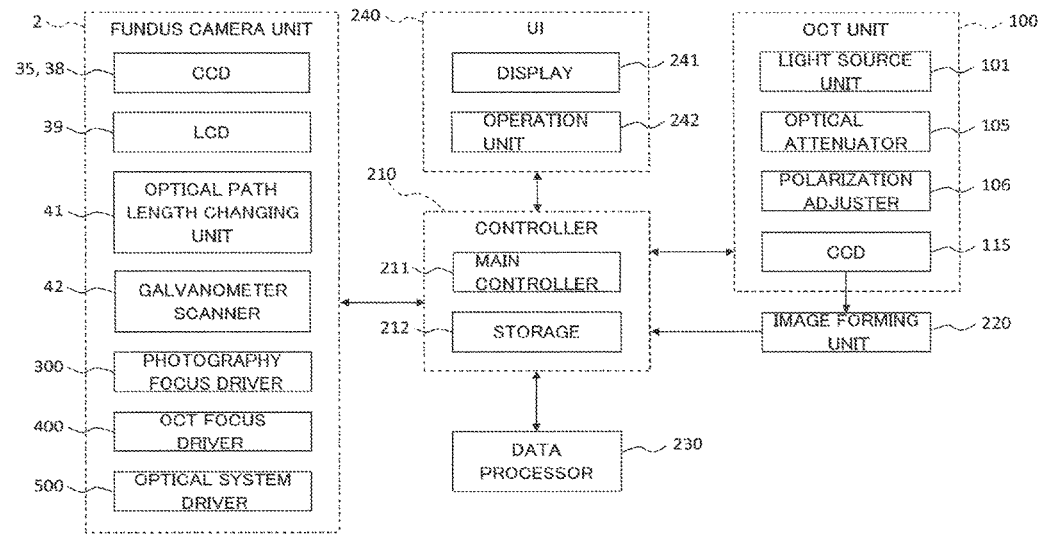
FIG. 3 is a schematic block diagram illustrating an example of the configuration of the ophthalmologic imaging apparatus of the embodiment.
Figure 4:
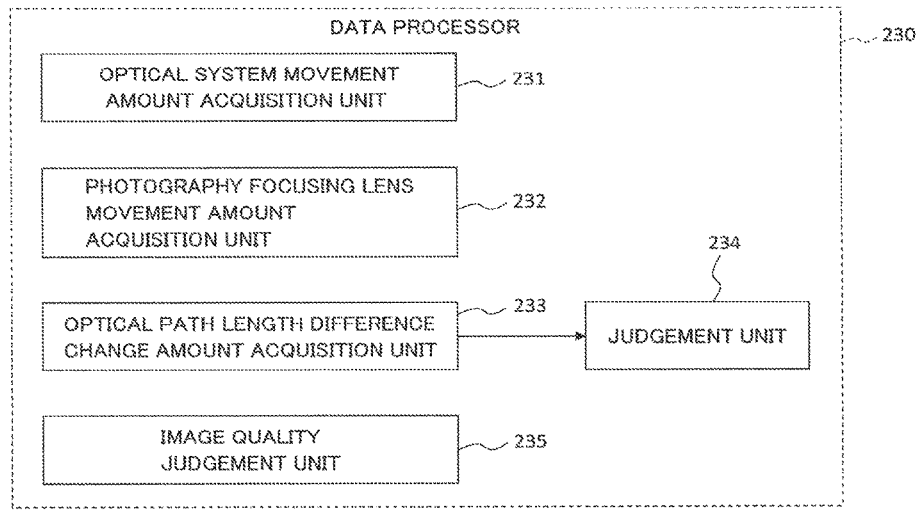
FIG. 4 is a schematic block diagram illustrating an example of the configuration of the ophthalmologic imaging apparatus of the embodiment.

The configuration of the control system of the ophthalmologic imaging apparatus 1 will be described with reference to FIGS. 3 and 4.

(Controller)

A controller 210 serves as the center of the control system of the ophthalmologic imaging apparatus 1. The controller 210 includes, for example, the aforementioned microprocessor, RAM, ROM, hard disk drive, a communication interface, and the like. The controller 210 is provided with a main controller 211 and storage 212.

(Main Controller)

The main controller 211 performs various types of controls mentioned above. In particular, the main controller 211 controls the components of the fundus camera unit 2, such as the optical path length changing unit 41, the galvanometer scanner 42, the focusing lens 31, the focus optical system 60 (photography focus driver 300), the focusing lens 43 (OCT focus driver 400), and whole optical system (optical system driver 500). Further, the main controller 211 controls the components of the OCT unit 100, such as the light source unit 101, the optical attenuator 105, and the polarization adjuster 106.

The photography focus driver 300 moves the focusing lens 31 in the direction along the optical axis of the imaging optical system 30, and moves the focus optical system 60 in the direction along the optical axis of the illumination optical system 10. Thereby, the focus position of the imaging optical system 30 is changed. The photography focus driver 300 may include a dedicated mechanism of moving the focusing lens 31 and a dedicated mechanism of moving the focus optical system 60. The photography focus driver 300 is controlled when focus adjustment is performed.

The OCT focus driver 400 moves the focusing lens 43 in the direction along the optical axis of the sample arm. This changes the focus position of the measurement light LS. The focus position of the measurement light LS corresponds to the depth position (z position) of the beam waist of the measurement light LS.

The optical system driver 500 three-dimensionally moves the optical system provided in the fundus camera unit 2. This control is used for operations such as alignment and tracking. Tracking is an operation to move the optical system of the apparatus according to eye movements of the eye E. To perform tracking, alignment and focus adjustment are performed in advance. In other words, tracking is a function of maintaining a suitable positional relationship in which alignment and focusing are matched by causing the position of the optical system of the apparatus to follow the eye movement. Further, the optical system driver 500 may be controlled to change the optical path length of the sample arm (therefore, to change the optical path length difference between the sample arm and the reference arm).

The main controller 211 performs writing of data into the storage 212, and readout of data from the storage 212.

The main controller 211 performs a plurality of preparatory operations prior to OCT measurement. The preparatory operations may include any one or more of alignment, rough focus adjustment, optical path length difference adjustment, polarization adjustment, and fine focus adjustment. The plurality of preparatory operations is performed in a predetermined order. In the present embodiment, alignment, rough focus adjustment, optical path length difference adjustment, polarization adjustment, and fine focus adjustment are performed in this order.

The types and order of the preparatory operations are not so limited, and they may be optional. For example, the preparatory operations may include small-pupil judgement. The small-pupil judgement is a preparatory operation to judge whether the pupil of the eye E is small (whether the eye E is microcoria). The small-pupil judgement may be performed between the rough focus adjustment and the optical path length difference adjustment. The small-pupil judgement includes, for example, a series of processes as follows: acquiring a front image (anterior segment image) of the eye E; specifying an image area (pupil area) corresponding to the pupil of the eye E; calculating the size (e.g., diameter, circumference length) of the pupil area; judging whether the pupil of the eye E is small based on the size calculated (threshold processing); controlling the diaphragm 19 when judged that the pupil of the eye E is small. Here, the calculation of the size of the pupil area may include circular or elliptic approximation of the pupil area.

The rough focus adjustment is a kind of focus adjustment using the split indicator described above. The rough focus adjustment may be performed by determining the position of the focusing lens 31 based on preliminary prepared information in which eye refractive powers and positions of the focusing lens 31 and based on a measured value of the refractive power of the eye E.

On the other hand, the fine focus adjustment is performed on the basis of interference sensitivity of OCT measurement. For example, the fine focus adjustment may be performed by: monitoring interference intensity (interference sensitivity) by performing OCT measurement of the eye E to acquire interference signals; searching the position of the focusing lens 43 so as to maximize the interference intensity; and moving the focusing lens 43 to the position searched.

The optical path length difference adjustment is performed by controlling the optical path length changing unit 41 so as to render the target site in a predetermined z position in the image frame of an OCT image. This corresponds to adjustment of the optical path length difference between the sample arm and the reference arm. The target site (which is used as a reference for the optical path length difference adjustment) may be set in advance to a site which is represented with characteristic brightness values in the OCT image, or a site which is represented with characteristic intensities in the reflection intensity profile. In a specific example, the reference for the optical path length difference adjustment may be set to the retinal pigment epithelium layer for fundus OCT, while the reference may be set to the corneal surface for anterior segment OCT. Such automatic processing to search proper optical path length difference is referred to as "auto-Z".

The optical path length difference adjustment is not limited to the auto-Z. For example, automatic processing to maintain the proper image-rendering position achieved through the auto-Z may be performed. Such processing is referred to as "Z-lock". To perform the Z-lock, the optical path length changing unit 41 is controlled so as to maintain a state in which the target site (which is used as a reference for the optical path length difference adjustment) is rendered in a predetermined z position in image frames.

There are cases in which the Z-lock cannot be performed properly due to body motion, eye movement, pulsation, or the like. That is, there is a possibility of failure in the Z-lock due to large misalignment of the optical system with respect to the eye E. A preparatory operation for coping with the possibility may be performed. This preparatory operation includes a process of changing the z position which is used as the reference for the Z-lock (i.e., the predetermined z-position described above). A specific example of the process of changing the z position (Z-lock position change processing) will be described later.

To perform the polarization adjustment, the polarization state of the reference light LR is adjusted for optimizing the interference efficiency between the measurement light LS and the reference light LR.

(Storage)

The storage 212 stores various types of data. Examples of the data stored in the storage 212 include image data of OCT images, image data of fundus images, and subject's eye information. The subject's eye information includes information related to a subject such as patient ID and name, information related to the subject's eye such as identification information of left eye/right eye, or the like. The storage 212 further stores various types of computer programs and data to run the ophthalmologic imaging apparatus 1.

(Image Forming Unit)

An image forming unit 220 forms image data of tomographic images of the fundus Ef based on detection signals from the CCD image sensor 115. As in conventional spectral-domain OCT, the image forming process includes noise removal (noise reduction), filtering, dispersion compensation, fast Fourier transform (FFT), and the like. When another type of OCT is employed, the image forming unit 220 performs known processing according to the type of OCT.

The image forming unit 220 includes, for example, the aforementioned circuit boards for forming OCT images. Incidentally, "image data" and "image" based on the image data may be treated in the same way in this specification.

(Data Processor)

The data processor 230 processes data acquired through photography of the eye E or data acquired through OCT measurement. For example, the data processor 230 performs various image processing and image analysis on OCT images formed by the image forming unit 220. The data processor 230 performs various types of image corrections such as brightness correction. The data processor 230 performs various image processing and image analysis on images (fundus images, anterior segment images, etc.) captured by the fundus camera unit 2.

The data processor 230 performs known image processing such as interpolation for interpolating pixels in tomographic images to form three-dimensional image data of the fundus Ef. The three-dimensional image data refers to image data in which positions of pixels are defined by a three-dimensional coordinate system. Examples of the three-dimensional image data include image data composed of three-dimensional arrays of voxels. Such image data is referred to as volume data or voxel data. To display an image based on volume data, the data processor 230 performs image rendering (e.g., volume rendering, maximum intensity projection (MIP)) on the volume data to form image data of a pseudo three-dimensional image taken from a specific view direction. The pseudo three-dimensional image is displayed on a display device such as a display 241.

The three-dimensional image data may be stack data of a plurality of tomographic images. The stack data is image data formed by three-dimensionally arranging tomographic images along a plurality of scan lines based on positional relationship of the scan lines. That is, the stack data is image data formed by representing tomographic images, which are originally defined in their respective two-dimensional coordinate systems, by a single three-dimensional coordinate system. That is, the stack data is image data formed by embedding tomographic images into a single three-dimensional space.

The data processor 230 includes an optical system movement amount acquisition unit 231, a photography focusing lens movement amount acquisition unit 232, an optical path length difference change amount acquisition unit 233, a judgement unit 234, and an image quality judgement unit 235. The optical system movement amount acquisition unit 231 is used for alignment. The photography focusing lens movement amount acquisition unit 232 is used for rough focus adjustment. The optical path length difference change amount acquisition unit 233 is used for auto-Z, Z-lock and Z-lock position change processing. The judgement unit 234 is used for Z-lock position change processing. The image quality judgement unit 235 is used for polarization adjustment and rough focus adjustment. The data processor 230 may include part of the components (units 231 to 235). It is sufficient that one or more of the components required for preparatory operations to be performed in an embodiment are provided. When a preparatory operation other than these is to be performed in an embodiment, a component required for this preparatory operation is provided. Incidentally, at least Z-lock and Z-lock position change processing are performed in the present embodiment, and at least components required for Z-lock and Z-lock position change processing are provided.

(Optical System Movement Amount Acquisition Unit)

When performing alignment, the ophthalmologic imaging apparatus 1 captures images of the eye E (images of the anterior segment) on which the alignment indicator is being projected to acquire front images. The front images form a moving image of a predetermined frame rate. The optical system movement amount acquisition unit 231 analyzes the front images (frames of the moving image) to acquire movement amount of the optical system required for achieving proper alignment state.

Information acquired by the optical system movement amount acquisition unit 231 is not limited to the movement amount of the optical system itself. The optical system movement amount acquisition unit 231 may acquire information substantially equivalent to the movement amount of the optical system, such as the contents of control of the optical system driver 500 (e.g., the number of pulses transmitted), or information obtained in the middle of the acquisition of the movement amount of the optical system (e.g., amounts of alignment errors).

Figure 5A:
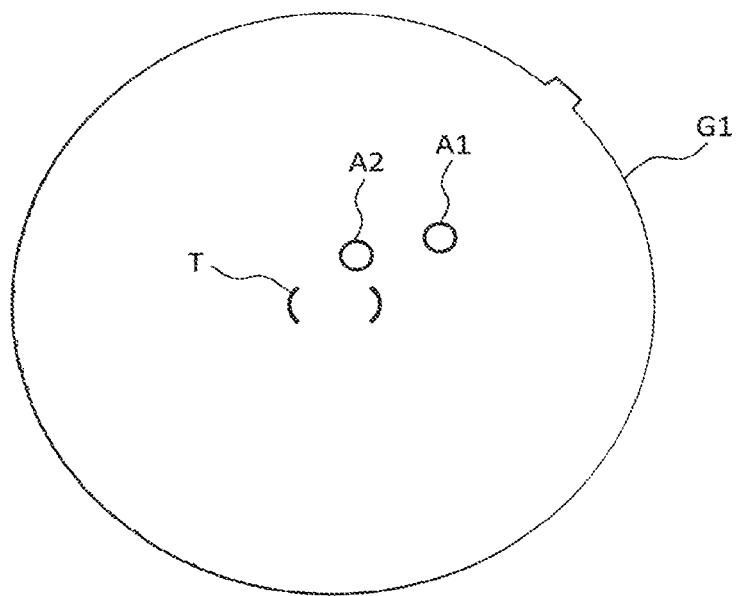
FIG. 5A is a schematic diagram for explaining the operation of the ophthalmologic imaging apparatus of the embodiment.
Figure 5B:
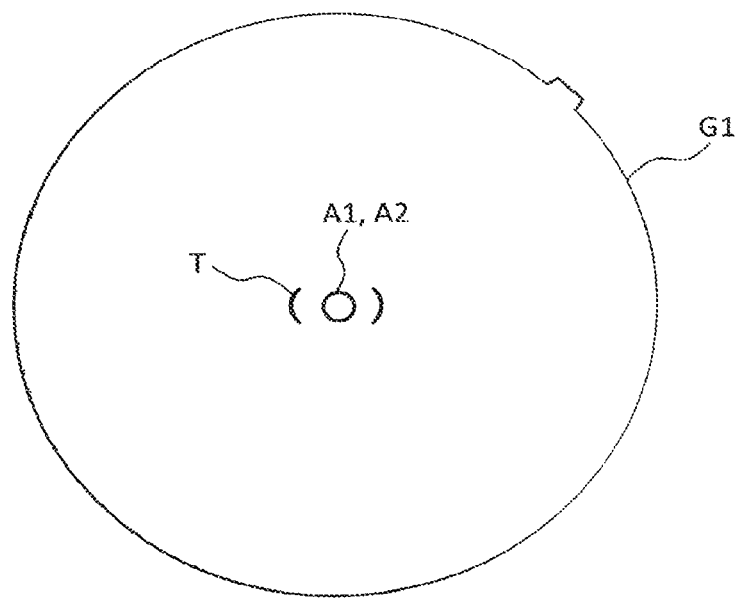
FIG. 5B is a schematic diagram for explaining the operation of the ophthalmologic imaging apparatus of the embodiment.

Examples of processing performed by the optical system movement amount acquisition unit 231 are described. The alignment indicator is depicted in front images fed to the optical system movement amount acquisition unit 231. Examples of aspects of the alignment indicator depicted are illustrated in FIGS. 5A and 5B. Images of the eye E are omitted in FIGS. 5A and 5B.

Two images A1 and A2 of the alignment indicator (alignment indicator images) are rendered, as bright spots, in a front image G1 of the eye E shown in FIG. 5A. The main controller 211 superimposes a target image T on the central area of the front image G1. The target image T is in the shape of a pair of parentheses, and indicates a target position for alignment.

When alignment state in the xy directions with respect to the eye E is not proper, the alignment indicator images A1 and A2 are rendered in positions away from the target image T. When alignment state in the z direction is not proper, the alignment indicator images A1 and A2 are rendered in positions different from each other. When alignment state in all of the xyz directions is proper, the alignment indicator images A1 and A2 are rendered one over another in the target image T as shown in FIG. 5B.

The displacements of the alignment indicator images A1 and A2 with respect to the target image T (amounts of the displacements, directions of the displacements) indicate alignment errors in the xy directions (amounts of the errors, directions of the errors). The displacement between the alignment indicator images A1 and A2 (amount of the displacement, direction of the displacement) indicates alignment errors in the z direction (amount of the error, direction of the error).

The optical system movement amount acquisition unit 231 analyzes the front image G1 to calculate alignment errors, and acquires movement amount of the optical system to cancel the alignment errors. Such processing may be processed in the following manner, for example. First, based on pixel information (brightness values etc.) of the front image G1, the optical system movement amount acquisition unit 231 specifies image areas corresponding to the alignment indicator images A1 and A2. Next, the optical system movement amount acquisition unit 231 specifies a characteristic position (center, center of gravity, etc.) of each of the image areas specified. Subsequently, the optical system movement amount acquisition unit 231 calculates the displacement of the characteristic position of each of the image areas from the central position of the target image T. Then, the optical system movement amount acquisition unit 231 calculates alignment errors based on the displacements calculated, and acquires movement amount of the optical system to cancel the alignment errors calculated. Note that the optical system movement amount acquisition unit 231 may include association information which associates displacements of alignment indicator images defined in a coordinate system of front images with alignment errors defined in a coordinate system of the real space, and may acquire alignment errors by referring to the association information. Operations for alignment are continued until amounts of the alignment errors calculated become equal to or smaller than a predetermined threshold.

(Photography Focusing Lens Movement Amount Acquisition Unit)

When performing rough focus adjustment, the ophthalmologic imaging apparatus 1 captures images of the fundus Ef on which the split indicator (focus indicator) is being projected to acquire front images. The front images form a moving image of a predetermined frame rate. The photography focusing lens movement amount acquisition unit 232 analyzes the front images (frames of the moving image) to acquire movement amount of the focusing lens 31 required for achieving proper focus state.

Information acquired by the photography focusing lens movement amount acquisition unit 232 is not limited to the movement amount of the focusing lens 31 itself. The photography focusing lens movement amount acquisition unit 232 may acquire information substantially equivalent to the movement amount of the focusing lens 31, such as the contents of control of the photography focus driver 300 (e.g., the number of pulses transmitted), or information obtained in the middle of the acquisition of the movement amount of the focusing lens 31 (e.g., amount of focus error).

Figure 6A:
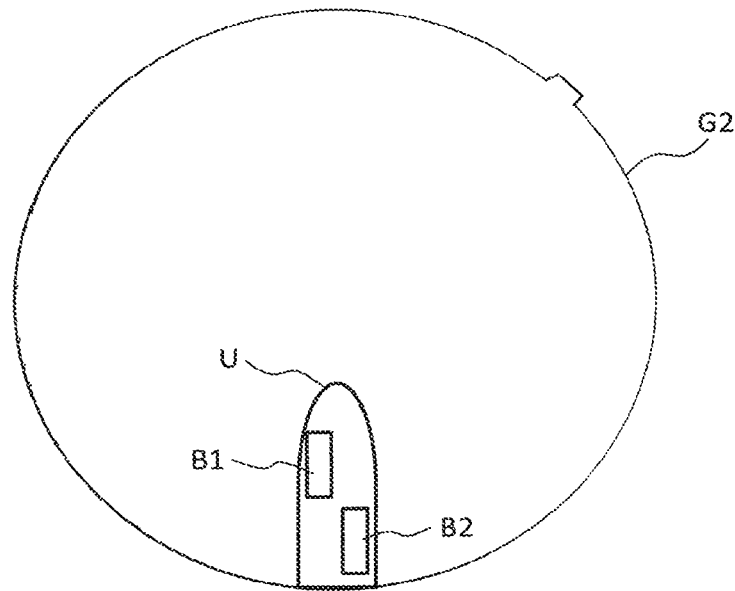
FIG. 6A is a schematic diagram for explaining the operation of the ophthalmologic imaging apparatus of the embodiment.
Figure 6B:
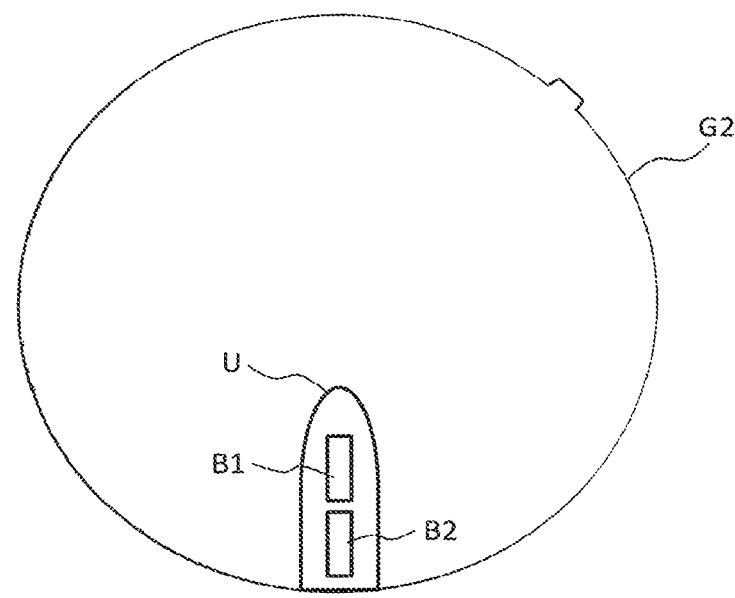
FIG. 6B is a schematic diagram for explaining the operation of the ophthalmologic imaging apparatus of the embodiment.

Examples of processing performed by the photography focusing lens movement amount acquisition unit 232 are described. The split indicator is depicted in front images fed to the photography focusing lens movement amount acquisition unit 232. Examples of aspects of the split indicator depicted are illustrated in FIGS. 6A and 6B. Images of the fundus Ef are omitted in FIGS. 6A and 6B.

The shadow of the reflection rod 67 is rendered in a front image G2 of the fundus Ef shown in FIG. 6A. In the shadow area, two images B1 and B2 of the split indicator (split indicator images) are rendered as bright lines.

When the focus position (in the z direction) is not proper, the split indicator images B1 and B2 are displaced, in the lateral direction, from each other. The direction of the displacement indicates the direction of the error in the focus position (+z direction or −z direction). The amount of the displacement indicates the magnitude of the error in the focus position. As shown in FIG. 6B, when the focus position is proper, the split indicator images B1 and B2 are substantially arranged in a straight vertical line.

The photography focusing lens movement amount acquisition unit 232 analyzes the front image G2 to calculate the error in the focus position, and acquires movement amount of the focusing lens 31 to cancel the error. Such processing may be processed in the following manner, for example. First, based on pixel information (brightness values etc.) of the front image G2, the photography focusing lens movement amount acquisition unit 232 specifies image areas corresponding to the split indicator images B1 and B2. Next, the photography focusing lens movement amount acquisition unit 232 specifies a characteristic position (center, center of gravity, axial line, etc.) of each of the image areas specified. Subsequently, the photography focusing lens movement amount acquisition unit 232 calculates the displacement, in the lateral direction, between the characteristic positions of the image areas corresponding to the split indicator images B1 and B2. Then, the photography focusing lens movement amount acquisition unit 232 calculates the error in the focus position based on the displacement calculated, and acquires movement amount of the focusing lens 31 to cancel the error in the focus position calculated. Note that the photography focusing lens movement amount acquisition unit 232 may include association information which associates displacements between split indicator images defined in a coordinate system of front images with focus position errors defined in a coordinate system of the real space, and may acquire a change amount in the focus position by referring to the association information.

The photography focusing lens movement amount acquisition unit 232 may be configured to acquire the movement amount of the focusing lens 43 in the sample arm. To acquire the movement amount, the photography focusing lens movement amount acquisition unit 232 may refer to association information similar to the one described above, or may refer to another association information that associates focus positions of the focusing lens 31 with those of the focusing lens 43. Focus adjustment of the sample arm performed in this way is rough adjustment. After the rough adjustment, fine adjustment is performed. Operations for rough focus adjustment are continued until the amount of the error in the focus adjustment calculated becomes equal to or smaller than a predetermined threshold.

(Optical Path Length Difference Change Amount Acquisition Unit and Judgement Unit)

When performing auto-Z, the ophthalmologic imaging apparatus 1 controls the optical system to perform OCT measurement of the fundus Ef. The OCT measurement repeatedly scans substantially the same cross section of the fundus Ef at a predetermined repetition rate. In other words, in the OCT measurement, iterative scan is performed to the eye E, to which a fixation target is presented, with the same scan pattern. The optical path length difference change amount acquisition unit 233 analyzes detection results of interference light LC (reflection intensity profiles, OCT images, etc.) repeatedly acquired by the OCT measurement to obtain change amount of the optical path length difference for positioning an image of the fundus Ef in a specific position in an image frame. The optical path length difference change amount acquisition unit 233 of the present embodiment is configured to acquire change amount of the optical path length of the sample arm.

Information acquired by the optical path length difference change amount acquisition unit 233 is not limited to the amount of the optical path length difference itself (or the amount of the optical path length itself). The optical path length difference change amount acquisition unit 233 may acquire information substantially equivalent to the movement amount of the optical path length difference, such as the contents of control of the optical path length changing unit 41 (e.g., the number of pulses transmitted), or information obtained in the middle of the acquisition of the movement amount of the optical path length difference (e.g., amount of z-directional shift of an image in an image frame).

Figure 7A:
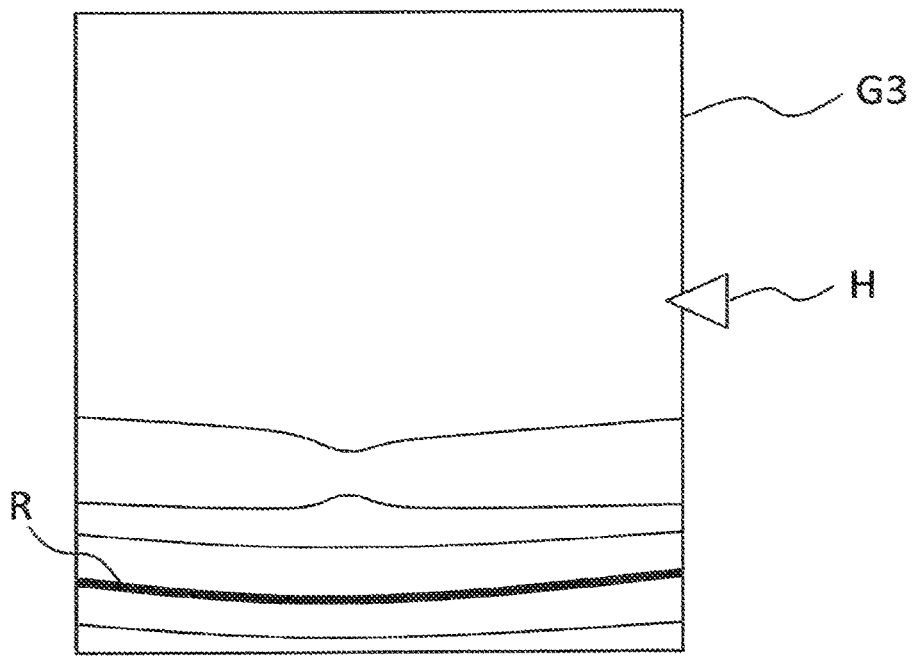
FIG. 7A is a schematic diagram for explaining the operation of the ophthalmologic imaging apparatus of the embodiment.

Examples of processing for auto-Z performed by the optical path length difference change amount acquisition unit 233 are described. When performing auto-Z, an OCT image G3 illustrated in FIG. 7A is displayed as a moving image. A slider H is displayed on the right side of the OCT image G3. The slider H can be moved vertically. A position indicated by the slider H corresponds to the specific position described above that is a target position for auto-Z. The position of the slider H may be any of a default position, a desired position set by a user, and a position changed through Z-lock position change processing.

Generally, in the initial stage of auto-Z, an image of the fundus Ef is not rendered in an OCT image, or an image of the fundus Ef is rendered in a certain position in an OCT image as a result of rough focus adjustment described above (see FIG. 7A). The OCT image G3 formed by the image forming unit 220 is fed to the optical path length difference change amount acquisition unit 233. The optical path length difference change amount acquisition unit 233 analyzes pixel information (brightness values etc.) of the OCT image G3 to specify an image area R that corresponds to a predetermined site of the fundus Ef (e.g., retinal pigment epithelium layer). The optical path length difference change amount acquisition unit 233 then obtains the z coordinate value of the image area R. The z coordinate value of the image area R may be a z coordinate value of a characteristic position (e.g., center, end part, lowest end, or highest end) in the image area R. Alternatively, the z coordinate value of the image area R may be a statistic (e.g., average, mode, or median) obtained through statistical calculation from z coordinate values of two or more positions in the image area R.

In the case that the image area R is not specified, that is, in the case that the predetermined site of the fundus Ef is not rendered in the OCT image G3, a signal indicating this fact is sent to the controller 210. The main controller 211 receives the signal, and controls the optical path length changing unit 41 according to a predetermined algorithm to perform specification of the image area R again. Such a series of processes is repeated until successful specification of the image area R.

Figure 7B:
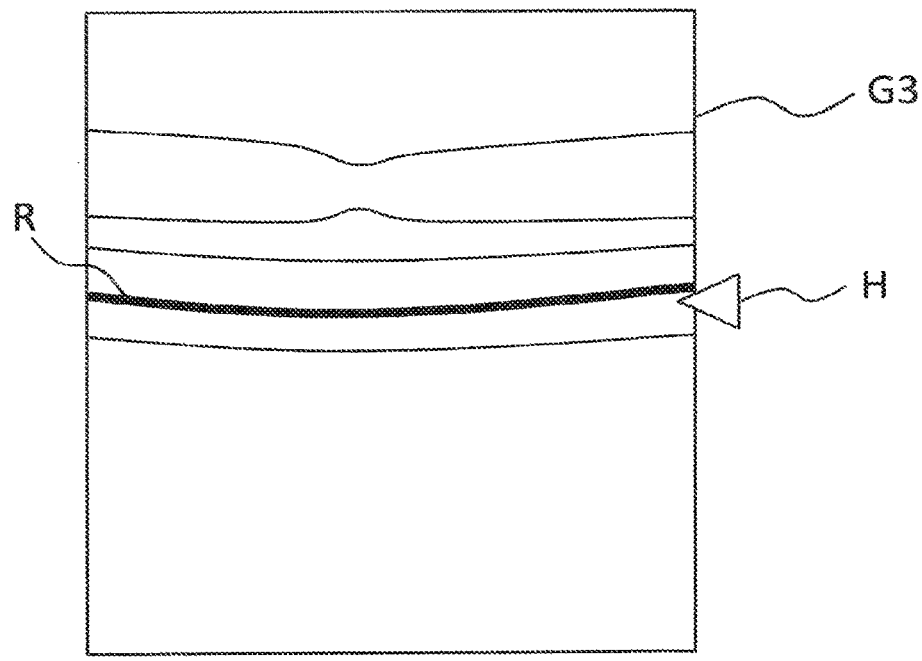
FIG. 7B is a schematic diagram for explaining the operation of the ophthalmologic imaging apparatus of the embodiment.

Once the image area R is specified and the z coordinate value of the image area R is obtained, the optical path length difference change amount acquisition unit 233 calculates the deviation of the z coordinate value of the image area R from the z coordinate value (reference z position) indicated by the slider H. The optical path length difference change amount acquisition unit 233 then acquires the amount of change in the optical path length difference to cancel the deviation calculated. Here, the optical path length difference change amount acquisition unit 233 may include association information which associates deviations in the z direction defined in a coordinate system of the OCT image G3 with errors in the optical path length difference defined in a coordinate system of the real space, and may acquire change amount of the optical path length difference by referring to the association information. FIG. 7B illustrates a state in which auto-Z has succeeded on the basis of the change amount thus acquired. Auto-Z is continued until the state illustrated in FIG. 7B is achieved, that is, until amount of the deviation calculated become equal to or smaller than a predetermined threshold.

Next, Z-lock will be described. As in auto-Z, Z-lock includes iterative scan of substantially the same cross section of the fundus Ef at a predetermined repetition rate. In addition, the optical path length difference change amount acquisition unit 233 analyzes detection results of interference light LC repeatedly acquired by this OCT measurement to obtain the amount of change in the optical path length difference for positioning the image area R in the reference z position indicated by the slider H. This processing is performed similarly to that in auto-Z.

Z-lock position change processing related to the optical path length difference change amount acquisition unit 233 and the judgement unit 234 will be described. Z-lock position change processing commences in response to the completion of auto-Z, and is performed concurrently with Z-lock. Z-lock position change processing includes: a process of monitoring the z-dimensional position of the image of the eye E (e.g., image area R or other image area) within the image frames of the OCT image G3; and a process of detecting the event that the image of the eye E has moved to the upper edges, the lower edges, or the outsides of the image frames.

As in auto-Z and Z-lock, Z-lock position change processing includes iterative scan of substantially the same cross section of the fundus Ef at a predetermined repetition rate.

Figure 8A:
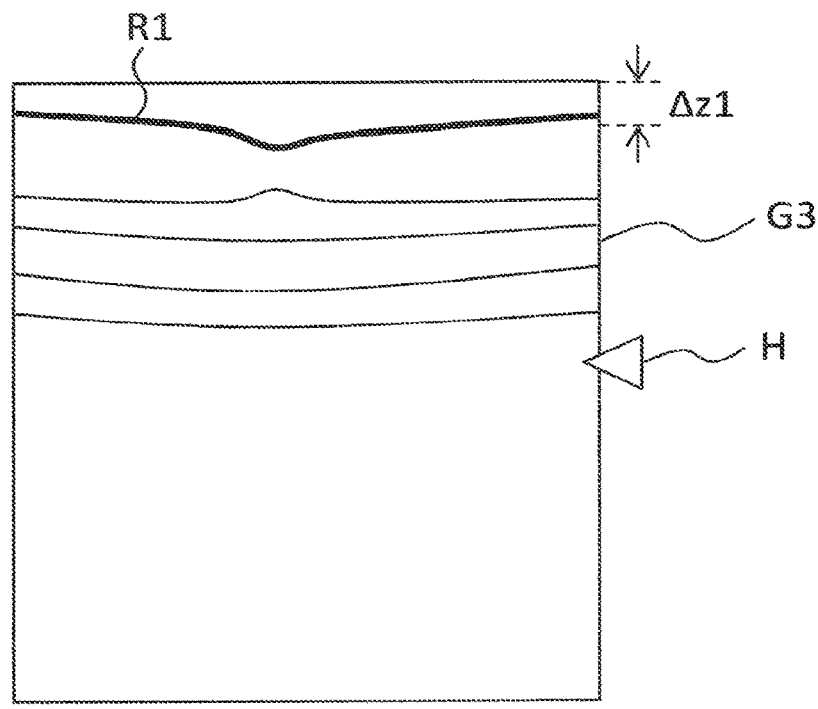
FIG. 8A is a schematic diagram for explaining the operation of the ophthalmologic imaging apparatus of the embodiment.

The optical path length difference change amount acquisition unit 233, for example, analyzes detection results of interference light LC repeatedly acquired by the OCT measurement to calculate the distance between the image of a predetermined site of the eye E and the upper edge (or the lower edge) of the image frame. In the example illustrated in FIG. 8A, the optical path length difference change amount acquisition unit 233 calculates the distance "Δz1" between an image area (surface area) R1 corresponding to the surface of the fundus Ef (i.e., the surface of the retina) and the upper edge of the image frame.

The judgement unit 234 is configured to judge whether the distance Δz1 calculated by the optical path length difference change amount acquisition unit 233 is equal to or less than a threshold. The threshold is set in advance. The threshold may be any value equal to or larger than zero. When the threshold is zero, the judgement unit 234 judges whether the surface area R1 meets the upper edge of the image frame. On the other hand, when the threshold is a positive value, the judgement unit 234 judges whether the surface area R1 comes near the upper edge of the image frame by a distance equal to or less than the threshold. Note that there may be cases where part or whole of the surface area R1 moves to the outside of the image frame. More specifically, the surface area R1 meets both the right and left edges of the image frame, in general. Examples of the cases described above include cases where the surface area R1 does not meet one or both of the right and left edges of the image frame, and cases where part or whole of the surface area R1 is not specified. In such cases, the judgement unit 234 can output the same judgement result as the case where the distance calculated by the optical path length difference change amount acquisition unit 233 is equal to or less than the threshold.

Figure 8B:
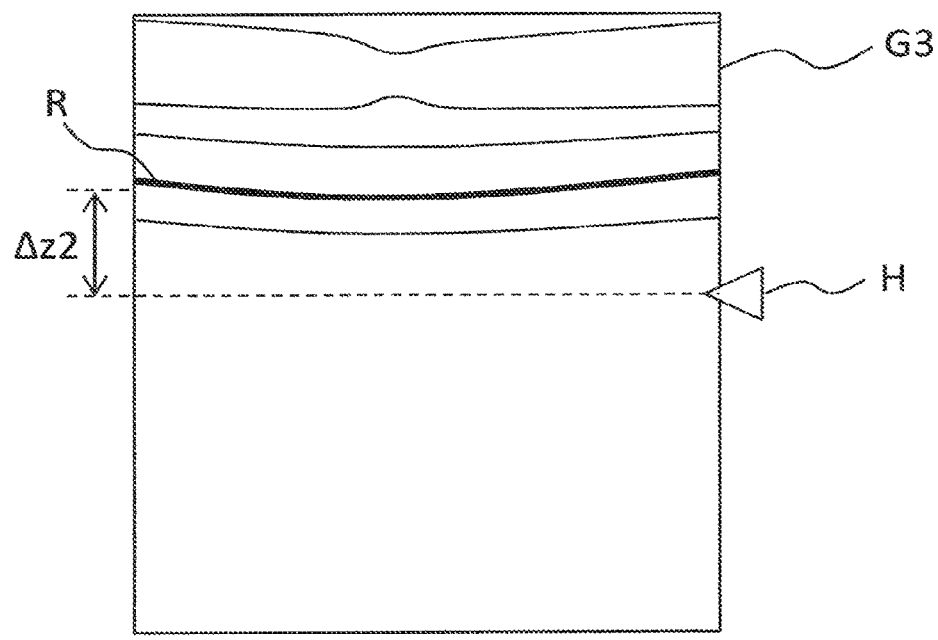
FIG. 8B is a schematic diagram for explaining the operation of the ophthalmologic imaging apparatus of the embodiment.

Another processing example will be described. The optical path length difference change amount acquisition unit 233 analyzes detection results of interference light LC repeatedly acquired by OCT measurement to calculate the distance between the image of a predetermined site of the eye E and the reference z position described above. In the example illustrated in FIG. 8B, the optical path length difference change amount acquisition unit 233 calculates the distance "Δz2" between an image area R corresponding to the retinal pigment epithelium layer and the reference z position indicated by the slider H.

The judgement unit 234 is configured to judge whether the distance Δz2 calculated by the optical path length difference change amount acquisition unit 233 is equal to or larger than a threshold. The threshold is set in advance. Note that there may be cases where part or whole of the image area R moves to the outside of the image frame. More specifically, the image area R meets both the right and left edges of the image frame, in general. Examples of the cases described above include cases where the image area R does not meet one or both of the right and left edges of the image frame, and cases where part or whole of the image area R is not specified. In such cases, the judgement unit 234 can output the same judgement result as the case where the distance calculated by the optical path length difference change amount acquisition unit 233 is equal to or larger than the threshold.

(Image Quality Judgement Unit)

Next, polarization adjustment will be described. When adjusting polarization state of measurement light LS and/or reference light LR, the ophthalmologic imaging apparatus 1 controls the polarization adjuster 106 according to a predetermined algorithm while performing iterative OCT measurement as described above. The image quality judgement unit 235 analyzes detection results of interference light LC repeatedly acquired by the OCT measurement to calculate a predetermined evaluation value relating to image quality of OCT images. Further, the image quality judgement unit 235 judges whether the evaluation value calculated is equal to or less than a threshold. The threshold is set in advance. Polarization adjustment is continued until the evaluation value calculated becomes equal to or less than the threshold.

Fine focus adjustment will be described. When performing fine focus adjustment, the ophthalmologic imaging apparatus 1 controls the OCT focus driver 400 according to a predetermined algorithm while performing iterative OCT measurement as described above. The image quality judgement unit 235 analyzes detection results of interference light LC repeatedly acquired by the OCT measurement to calculate a predetermined evaluation value relating to image quality of OCT images. Further, the image quality judgement unit 235 judges whether the evaluation value calculated is equal to or less than a threshold. Fine focus adjustment is continued until the evaluation value calculated becomes equal to or less than the threshold.

Incidentally, fine focus adjustment may be performed in other ways. For example, an ophthalmologic imaging apparatus may be configured to concurrently perform acquisition of interference signals through iterative OCT measurement as described above, and monitoring of intensities of the interference signals acquired one after another (i.e., monitoring of interference intensity or interference sensitivity). In addition, while performing the monitoring, the ophthalmologic imaging apparatus can move the focusing lens 43 to find the position of the focusing lens 43 in which the interference intensity is maximized. With the fine focus adjustment thus performed, the focusing lens 43 can be guided to the position where the interference intensity is optimized. Polarization adjustment may include similar interference intensity monitoring. More generally, any processing for real time optimization, such as polarization adjustment and fine focus adjustment, may be performed by referring to any kind of evaluation value that varies in association with change in an object (parameter) to be adjusted.

The data processor 230 having above functions includes, for example, a microprocessor, RAM, ROM, a hard disk drive, a circuit board, and the like. The storage device such as the hard disk drive stores, in advance, computer programs for causing the microprocessor to implement the above functions.

(User Interface)

A user interface 240 includes the display 241 and an operation unit 242. The display 241 includes the aforementioned display device in the arithmetic and control unit 200 and the display device 3. The operation unit 242 includes the aforementioned operation devices in the arithmetic and control unit 200. The operation unit 242 may include various types of buttons and keys provided on the case or the outside of the ophthalmologic imaging apparatus 1. For example, if the fundus camera unit 2 has a case similar to that of conventional fundus cameras, the operation unit 242 may include a joy stick, an operation panel, and the like provided on the case. Besides, the display 241 may include various types of display devices, such as a touch panel, provided on the case of the fundus camera unit 2.

The display 241 and the operation unit 242 need not necessarily be formed as separate devices. For example, a device like a touch panel, which has a display function integrated with an operation function, may be employed. In such cases, the operation unit 242 includes the touch panel and computer programs. Contents of operations performed using the operation unit 242 (electrical signals) are fed to the controller 210. Moreover, operations and inputs of information may be performed using a graphical user interface (GUI) displayed on the display 241 and the operation unit 242.

[Scan with Measurement Light and OCT Images]

Here, scan with measurement light LS and OCT images are described.

Examples of scan modes with measurement light LS performed by the ophthalmologic imaging apparatus 1 include horizontal scan, vertical scan, cross scan, radial scan, circle scan, concentric scan, helical (spiral) scan, and the like. These scan modes are selectively used in consideration of a site of eye fundus to be observed, an object to be analyzed (thickness of retina, etc.), time required for scan, accuracy of scan, or the like.

In the horizontal scan mode, measurement light LS is deflected in the horizontal direction (x direction). The horizontal scan mode includes scans with measurement light LS along a plurality of horizontal scan lines arranged in the vertical direction (y direction). In this mode, the intervals between the horizontal scan lines may be set as desired. The intervals of the horizontal scan lines may be set sufficiently small to form a three-dimensional image. Such a scan mode is referred to as three-dimensional scan. These items for the horizontal scan mode may be applied to the vertical scan mode in similar ways.

In the cross scan mode, measurement light LS is successively projected on a cruciform trajectory consisting of two straight lines which are perpendicular to each other. In the radial scan mode, measurement light LS is successively projected on radial trajectories consisting of a plurality of straight lines arranged at a predetermined angle. The cross scan mode is an example of the radial scan mode.

In the circle scan mode, measurement light LS is successively projected on a circular trajectory. In the concentric scan mode, the measurement light LS is successively projected on a plurality of circular trajectories arranged concentrically around a predetermined center position. The circle scan is an example of the concentric scan. In the helical scan mode, the measurement light LS is successively projected on a helical (spiral) trajectory while the rotation radius is gradually reduced (or increased).

The galvanometer scanner 42 is configured to deflect measurement light LS in directions perpendicular to each other, and therefore, is capable of deflecting measurement light LS in the x direction and the y direction independently of one another. Further, by controlling the orientations of two galvanometer mirrors included in the galvanometer scanner 42 at the same time, measurement light LS can be guided along an arbitrary trajectory on the xy plane. Thus, a variety of scan modes as described above can be implemented.

By performing scan with measurement light LS in the manner described above, the ophthalmologic imaging apparatus 1 acquires a tomographic image corresponding to a plane spanned by the axis along the scan lines (scan trajectories) and the axis along the depth direction of the fundus (z direction). Besides, particularly when the scan lines are arranged at narrow intervals, three-dimensional image as described above can be created.

An area on the fundus Ef to be scanned with measurement light LS as described above, that is, an area on the fundus Ef subjected to OCT measurement, is referred to as a "scan area". A scan area for the three-dimensional scan may be a rectangular area in which a plurality of horizontal scan lines is arranged. A scan area for the concentric scan may be a disc-shaped area surrounded by the trajectory of circle scan with the largest diameter. In addition, a scan area for the radial scan is a disc-shaped (or polygonal) area surrounded by a line connecting the ends of the scan lines.

Operation Example

Figure 9:
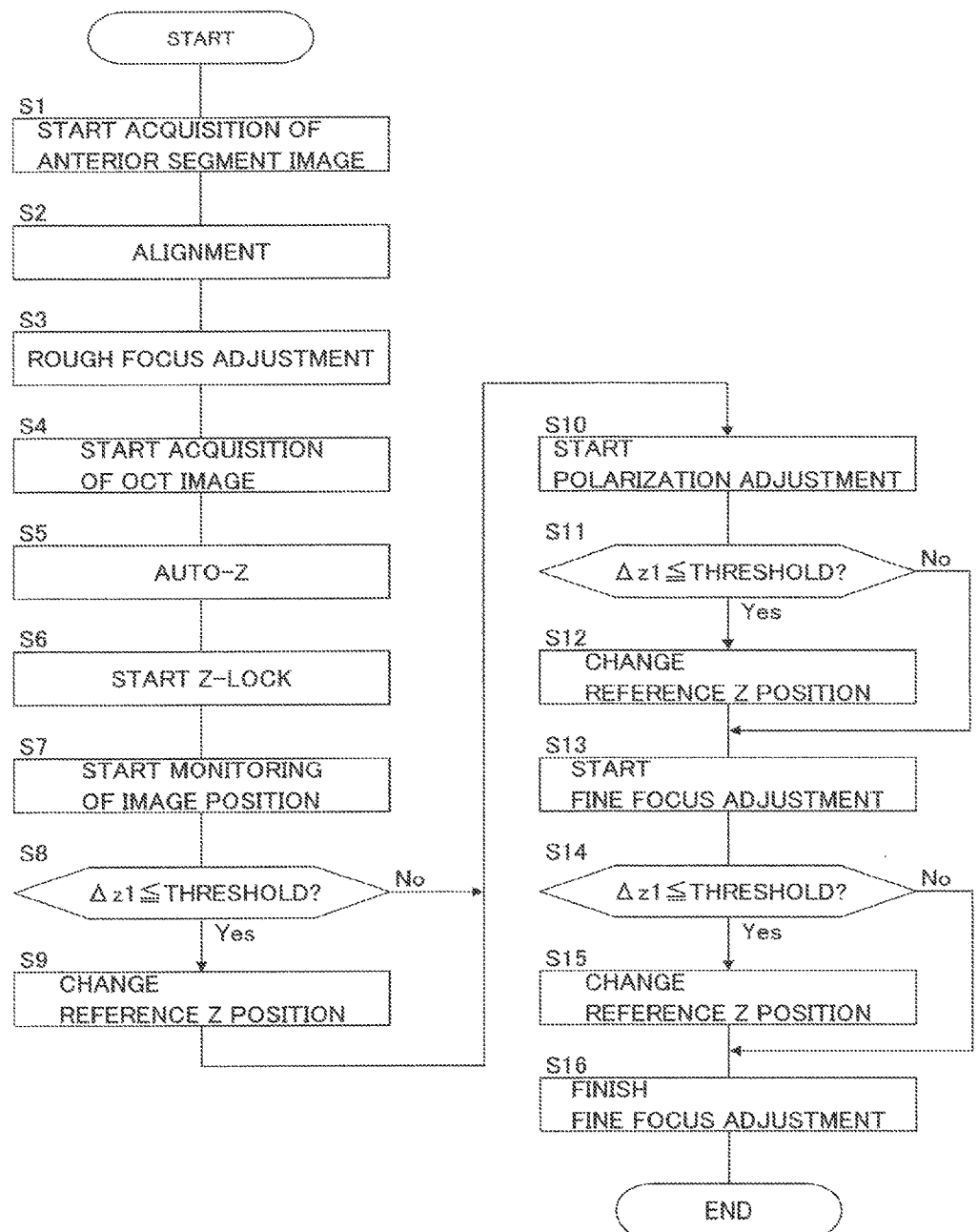
FIG. 9 is a flowchart illustrating an example of the operation of the ophthalmologic imaging apparatus of the embodiment.

Operations of the ophthalmologic imaging apparatus 1 will be described. FIG. 9 shows an example of processing executed by the ophthalmologic imaging apparatus 1 for preparatory operations performed before OCT measurement (and before fundus photography). In this example, a case will be described where preliminary operations are performed in the order of alignment, rough focus adjustment, auto-Z, Z-lock, Z-lock position change processing, polarization adjustment and fine focus adjustment.

(S1: Start Acquisition of Anterior Segment Image)

First, the main controller 211 turns on the observation light source 11 in response to a predetermined operation for starting the preliminary operations. As a result, acquisition of front images (near-infrared moving image) of the anterior segment of the eye E is started. The front images are obtained in real time until the observation light source 11 is turned off. The main controller 211 displays the front images on the display unit 241 in real time as a moving image.

(S2: Alignment)

The main controller 211 controls the alignment optical system 50 to project the alignment indicator on the eye E. At this time, a fixation target generated by the LCD 39 is also projected onto the eye E. The optical system movement amount acquisition unit 231 analyzes frames (for example, all frames) acquired at predetermined time intervals, and acquires the movement amount of the optical system. The main controller 211 controls the optical system driver 500 to move the optical system by the movement amount acquired. The main controller 211 repeatedly performs this processing.

(S3: Rough Focus Adjustment)

When the alignment is completed, the main controller 211 starts the rough focus adjustment. Specifically, the main controller 211 starts acquiring the front images of the fundus Ef, and controls the focus optical system 60 to project the split indicator on the fundus Ef. The photography focusing lens movement amount acquisition unit 232 analyzes frames (for example, all frames) acquired at predetermined time intervals, and acquires the movement amount of the focusing lens 31. The main controller 211 controls the photography focus driver 300 to move the focusing lens 31 by the movement amount acquired. Here, when the photography focusing lens movement amount acquisition unit 232 also acquires the movement amount of the focusing lens 43, the main controller 211 controls the OCT focus driver 400 to move the focusing lens 43 by this movement amount acquired. The main controller 211 repeatedly executes this processing.

Note that when the small-pupil judgement described above is performed, the main controller 211 performs the small-pupil judgement in response to the completion of the rough focus adjustment.

(S4: Start Acquisition of OCT Image)

Upon receiving the completion of the rough focus adjustment (or the small-pupil judgement), or upon receiving a predetermined instruction input after the completion of the rough focus adjustment (or the small-pupil judgement), the main controller 211 causes the OCT measurement to be started. As described above, in this OCT measurement, substantially the same cross section of the fundus Ef is repeatedly scanned at a predetermined repetition rate.

(S5: Auto-Z)

Based on OCT images (or reflection intensity profiles etc.), acquisition of which is started in Step 4, the main controller 211 performs the auto-Z.

(S6: Start Z-Lock)

Upon receiving the completion of the auto-Z, the main controller 211 causes the Z-lock to be started.

(S7: Start Monitoring of Image Position)

As the Z-lock is started, the main controller 211 starts monitoring for changing the Z-lock position. In this monitoring process, as described above, the position in the z direction of the image (e.g., the image area R or the surface area R1) of the eye E in the image frames of OCT images is monitored. In the present example, the case will be described where the distance $\Delta z1$ between the surface area R1 corresponding to the surface of the retina and the upper edge of the image frame is calculated. Similar processing can be employed in other cases (for example, in the case where the above distance $\Delta z2$ is calculated).

(S8: Distance $\Delta z1$=Threshold or $\Delta z1$<Threshold?)

As described above, the judgement unit 234 judges whether the distance $\Delta z1$ is equal to the threshold or less than the threshold. When the polarization adjustment (S10) starts without having been judged that the distance $\Delta z1$ is equal to or smaller than the threshold (S8: No), processing of the present operation example goes on.

(S9: Change Reference z Position)

On the other hand, when it is determined that the distance $\Delta z1$ is equal to or smaller than the threshold before the polarization adjustment (S10) is started (S8: Yes), the main controller 211 changes the current reference z position to a new reference z position. This processing corresponds to the change of the position of the slider H shown in FIG. 7A. The new reference z position is located, for example, on the upper edge side of the image frame than the current reference z position. Also, the distance between the current reference z position and the new reference z position may be, for example, the same as the displacement amount of the image with respect to the current reference z position. The displacement amount is acquired, for example, as a displacement between the reference z position and the image area R. Even after the reference z position is changed, the process of step S7 and the process of step S8 continue. If the process of step S8 obtains the result "Yes" again, the reference z position is changed again.

(S10: Start Polarization Adjustment)

Upon receiving a transition trigger to the polarization adjustment, the main controller 211 causes the polarization adjustment to be started. Also in this stage, the monitoring process started in step S7 is executed in parallel.

(S11: Distance $\Delta z1$=Threshold or $\Delta z1$<Threshold?)

The judgement unit 234 judges whether the distance $\Delta z1$ is equal to or less than the threshold. When the polarization adjustment is completed without having been judged that the distance $\Delta z1$ is equal to or less than the threshold (S11: No), the process proceeds to step S13.

(S12: Change Reference z Position)

On the other hand, when it is judged that the distance $\Delta z1$ is equal to or smaller than the threshold before the completion of the polarization adjustment (S11: Yes), the main controller 211 changes the current reference z position to a new reference z position. This process may be performed in the same way as in step S9.

(S13: Start Fine Focus Adjustment)

Upon receiving a transition trigger to the fine focus adjustment, the main controller 211 starts the focus fine adjustment. Also in this stage, the monitoring process started in step S7 is executed in parallel.

(S14: Distance $\Delta z1$=Threshold or $\Delta z1$<Threshold?)

The judgement unit 234 judges whether the distance $\Delta z1$ is equal to or less than the threshold. When the fine focus adjustment is completed without having been judged that the distance $\Delta z1$ is equal to or less than the threshold (S14: No, S16), the preparatory operations are ended, and the state of the ophthalmologic imaging apparatus 1 is transferred to a state capable of performing OCT measurement of the fundus E.

(S15: Change Reference z Position)

On the other hand, when it is judged that the distance $\Delta z1$ is equal to or smaller than the threshold before the completion of the fine focus adjustment (S14: Yes), the main controller 211 changes the current reference z position to a new reference z position. This process may be performed in the same way as in step S9.

(S16: Finish Fine Focus Adjustment)

Upon completion of the fine focus adjustment, all the preparatory operations are completed, and the state of the ophthalmologic imaging apparatus 1 shifts to a state in which OCT measurement of the fundus Ef can be performed.

Effects

A description is given of effects of the ophthalmologic imaging apparatus of the embodiment.

The ophthalmologic imaging apparatus of the embodiment includes a configuration to repeatedly acquire data of an eye by repeatedly scanning the eye using OCT. This configuration includes an interference optical system for performing OCT. The interference optical system includes a light source unit (101), a sample arm configured to guide measurement light (LS), a reference arm configured to guide reference light (LR), and a detector (spectrometer, balanced photodiode, etc.) configured to detect interference light (LC). Further, a component (image forming unit 220 etc.) configured to process detection results of the interference light is provided. Such a configuration corresponds to an example of data acquisition unit.

In addition, the ophthalmologic imaging apparatus of the embodiment includes a controller configured to perform first control and second control. In the first control, the controller adjusts optical path length difference between the sample arm and the reference arm so as to place an image of the eye in a reference position (reference z position) in an image frame based on the data repeatedly acquired by the data acquisition unit. The first control includes, for example, auto-Z and Z-lock. In the second control, the controller changes the optical path length difference between the sample arm and the reference arm so as to place the image of the eye in a new reference position (new reference z position) in the image frame based on the data repeatedly acquired by the data acquisition unit. In the above embodiment, the controller that performs these controls includes the controller 210 and further includes part of the data processor 230.

According to the embodiment thus configured, even when a site of interest is rendered near the edge of the image frame or located outside of the image frame due to the movement of the eye, the reference position can be automatically changed to render the site of interest in a suitable position. Further, a rendering position of the site of interest can be automatically corrected before the site of interest becomes to be rendered in unsuitable positions. Therefore, the embodiment is capable of properly performing preparatory operations for OCT measurement of the subject's eye, and of acquiring an OCT image in which the site of interest is rendered in a suitable position in the image frame.

In the embodiment, the controller may include a judgement unit. The judgement unit is configured to judge whether to perform the second control based on the data repeatedly acquired by the data acquisition unit when one or more preparatory operations for OCT measurement of the eye are being performed. In the above embodiment, the judgement unit includes part of the data processor 230. Examples of the preparatory operations include polarization adjustment to adjust the polarization state of measurement light and/or the polarization state of reference light, and fine focus adjustment to adjust focus state of the sample arm.

With the embodiment thus configured, the reference position can be automatically adjusted in parallel with the preparatory operations performed before OCT measurement of the eye.

In the embodiment, the judgement unit may include a first distance calculation unit (optical path length difference change amount acquisition unit 233) and a first distance judgement unit (judgement unit 234). The first distance calculation unit is configured to calculate distance between an image of a predetermined site of the eye and an upper edge or a lower edge of the image frame. The first distance judgement unit is configured to judge whether the calculated distance is equal to or less than a preset threshold. Further, the controller may be configured to perform the second control when the first distance judgement unit has judged that the distance is equal to or less than the threshold.

In a specific example of the embodiment thus configured, the threshold may be set to zero. In another specific example, the predetermined site may be the surface of the retina of the eye, and the first distance calculation unit may be configured to calculate distance between the image of the retinal surface and the upper edge of the image frame. Optionally, the controller may be configured to perform the second control so as to set the new reference position between the current reference position and the upper edge of the image frame.

In the embodiment, the judgement unit may include a second distance calculation unit (optical path length difference change amount acquisition unit 233) and a second distance judgement unit. (judgement unit 234). The second distance calculation unit is configured to calculate distance between an image of a predetermined site of the eye and the reference position. The second distance judgement unit is configured to judge whether the calculated distance is equal to or larger than a preset threshold. Further, the controller may be configured to perform the second control when the second distance judgement unit has judged that the distance is equal to or larger than the threshold.

In a specific example of the embodiment thus configured, the controller may be configured to perform the second control so as to set the new reference position in a position in a direction to which the image of the predetermined site is displaced. In another specific example, the predetermined site may be a predetermined layer of the retina of the eye (e.g., retinal pigment epithelium layer).

Examples of Modifications

The configurations described above are mere examples for embodying or carrying out the present invention, and therefore susceptible to several modifications and variations (omission, substitution, addition, etc.), all come within the scope of the invention.

In the above embodiment, the reference z position is changed so that the site of interest (e.g., the retinal pigment epithelium layer) is placed in a suitable position within the image frame; however the present invention is not so limited. For example, an ophthalmologic imaging apparatus may be configured to change the reference z position so as to move the image of a site unnecessary for observation and/or the image obstructing observation to the vicinity of the edge of the image frame or the outside of the image frame. Such processing may include: a process of specifying a predetermined image area by analyzing OCT images and reflection intensity profiles; a process of obtaining the movement amount of the reference z position for moving the specified image area to the vicinity of the edge of the image frame or the outside of the image frame; and a process of changing the optical path length difference between the sample arm and the reference arm based on the obtained movement amount.

A specific example will be described in which a mirror image is included in an OCT image with reference to the configuration of the above embodiment. In this example, the iterative OCT measurement described in the above embodiment is performed. Image frames are sequentially input to the data processor 230, and the data processor 230 (mirror image specification unit) analyzes the frames to specify image areas (mirror image areas) corresponding to mirror images. Further, for each of the image frames, the data processor 230 calculates the distance between the mirror image area and a predetermined edge area (a one-dimensional, two-dimensional or three-dimensional area including at least the upper edge or the lower edge of the image frame). The distance includes at least the distance in the z direction. Further, the position of the mirror image area may be defined to be the position of any location in the mirror image area. For example, when moving the mirror image area to the upper edge side of the image frame, the position of the mirror image area may be defined to be the position of the lower edge of the mirror image area. In this case, the entire mirror image area can be moved to the edge area). The main controller 211 moves the reference z position by the obtained distance. With this, the second control can be executed so as to place the mirror image area in a new reference position located in the vicinity of the edge of the image frame or the outside of the image frame. Therefore, it is possible to avoid the situation where the mirror image area obstructs the observation.

It is assumed that it is difficult to achieve compatibility between the second control according to the above embodiment and the second control according to the present modification. For example, there may be a case where a mirror image appears on the site of interest. In such a case, any one of the second control according to the above embodiment and the second control according to the present modification may be prioritized. For example, it is possible to preferentially execute the second control according to the above embodiment, and to execute another process for removing, thinning, or moving the mirror image.

A computer program for realizing the above embodiment or the modification may be stored in any kind of readable computer recording medium. Examples of the recording medium include a semiconductor memory, an optical disk, a magneto-optical disk (CD-ROM, DVD-RAM, DVD-ROM, MO, etc.), a magnetic storage medium (hard disk, floppy (registered trade mark) disk, ZIP, etc.), and the like.

The computer program may be transmitted and received through a network such as the Internet, LAN, etc.

EXPLANATION OF SYMBOLS

Ophthalmologic imaging apparatus
Galvanometer scanner
100 OCT unit
101 Light source unit
115 CCD image sensor
210 Controller
220 Image forming unit
230 Data processor

The invention claimed is:

1. An ophthalmologic imaging apparatus, comprising:
a data acquisition unit configured to acquire data by scanning an eye using optical coherence tomography;
an image forming processor that forms an image from the data acquired by the data acquisition unit; and
a control processor that controls the data acquisition unit to repeatedly scan the eye to repeatedly acquire data, wherein
the data acquisition unit includes
a light source,
a beam splitter that splits light output from the light source into measurement light and reference light,
a sample arm that guides the measurement light to the eye and guides returning light of the measurement light from the eye,
a reference arm that guides the reference light,
a beam combiner that superposes the returning light guided by the sample arm with the reference light guided by the reference arm to generate interference light,
a light detector that detects the interference light generated by the beam combiner, and
an optical path length changing unit that changes at least one of an optical path length of the sample arm and an optical path length of the reference arm, and
the control processor performs first control of the optical path length changing unit to place an image of the eye in a reference position in a frame of an image formed by the image forming processor based on the data repeatedly acquired by the data acquisition unit, and second control of the optical path length changing unit to place an image of the eye in another reference position in a frame of an image formed by the image forming processor based on the data repeatedly acquired by the data acquisition unit.

2. The ophthalmologic imaging apparatus of claim 1, wherein the control processor comprises a judgement unit configured to judge whether to perform the second control based on the data repeatedly acquired by the data acquisition unit when one or more preparatory operations for optical coherence tomography of the eye are being performed.

3. The ophthalmologic imaging apparatus of claim 2, wherein the judgement unit comprises:
a first distance calculation unit configured to calculate distance between an image of a predetermined site of the eye and an upper edge or a lower edge of the image frame; and
a first distance judgement unit configured to judge whether the distance calculated by the first distance calculation unit is equal to or less than a preset threshold, and
the control processor is configured to perform the second control when the first distance judgement unit has judged that the distance is equal to or less than the threshold.

4. The ophthalmologic imaging apparatus of claim 3, wherein the threshold is set to zero.

5. The ophthalmologic imaging apparatus of claim 3, wherein the predetermined site is a surface of a retina of the eye, and
the first distance calculation unit is configured to calculate distance between an image of the surface of the retina and the upper edge of the image frame.

6. The ophthalmologic imaging apparatus of claim 5, wherein the control processor is configured to perform the second control so as to set the another reference position between the reference position and the upper edge of the image frame.

7. The ophthalmologic imaging apparatus of claim 2, wherein the judgement unit comprises:
a second distance calculation unit configured to calculate distance between an image of a predetermined site of the eye and the reference position; and
a second distance judgement unit configured to judge whether the distance calculated by the second distance calculation unit is equal to or larger than a preset threshold, and
the control processor is configured to perform the second control when the second distance judgement unit has judged that the distance is equal to or larger than the threshold.

8. The ophthalmologic imaging apparatus of claim 7, wherein the control processor is configured to perform the second control so as to set the another reference position in a position in a direction to which the image of the predetermined site is displaced.

9. The ophthalmologic imaging apparatus of claim 7, wherein the predetermined site is a predetermined layer of a retina of the eye.

10. The ophthalmologic imaging apparatus of claim 2, wherein the one or more preparatory operations include adjustment of a polarization state of at least one of the measurement light guided by the sample arm and reference light guided by the reference arm.

11. The ophthalmologic imaging apparatus of claim 2, wherein the one or more preparatory operations include focus adjustment of the sample arm.

12. The ophthalmologic imaging apparatus of claim 1, wherein the control processor comprises a mirror image specification unit configured to specify a mirror image of the eye included in the image frame, and
the control processor is configured to perform the second control so as to place the mirror image specified by the mirror image specification unit in the another reference position located in the vicinity of an edge of the image frame or located outside of the image frame.

13. A method of controlling an ophthalmologic imaging apparatus, the method comprising:
acquiring data, at a data acquisition unit, by scanning an eye using optical coherence tomography, the data acquisition unit including a light source, a beam splitter that splits light output from the light source into measurement light and reference light, a sample arm that guides the measurement light to the eye and guides returning light of the measurement light from the eye, a reference arm that guides the reference light, a beam combiner that superposes the returning light guided by the sample arm with the reference light guided by the reference arm to generate interference light, a light detector that detects the interference light generated by the beam combiner, and an optical path length changing unit that changes at least one of an optical path length of the sample arm and an optical path length of the reference arm;

forming an image, at an image forming processor, from data acquired by the acquiring data at the data acquisition unit;

controlling, by a control processor, the data acquisition unit to repeatedly scan the eye to repeatedly acquire data;

performing first control of the optical path length changing unit to place an image of the eye in a reference position in a frame of an image formed by the image forming processor based on the data repeatedly acquired by the data acquisition unit; and performing second control of the optical path length changing unit to place an image of the eye in another reference position in a frame of an image formed by the image forming processor based on the data repeatedly acquired by the data acquisition unit.

14. An ophthalmologic imaging apparatus, comprising:

a data acquisition unit configured to acquire data by scanning an eye using optical coherence tomography;

an image forming processor that forms an image from the data acquired by the data acquisition unit; and a control processor that controls the data acquisition unit to repeatedly scan the eye to repeatedly acquire data, wherein
the data acquisition unit includes
a light source,
a beam splitter that splits light output from the light source into measurement light and reference light,
a sample arm that guides the measurement light to the eye and guides returning light of the measurement light from the eye,
a reference arm that guides the reference light,
a beam combiner that superposes the returning light guided by the sample arm with the reference light guided by the reference arm to generate interference light,
a light detector that detects the interference light generated by the beam combiner, and
an optical path length changing unit that changes at least one of an optical path length of the sample arm and an optical path length of the reference arm, and
the optical path length changing unit changes at least one of the optical path length of the sample arm and the optical path length of the reference arm to place an image of the eye in a reference position in a frame of an image formed by the image forming processor under first control of the control processor based on the data repeatedly acquired by the data acquisition unit, and changes at least one of the optical path length of the sample arm and the optical path length of the reference arm to place an image of the eye in another reference position in a frame of an image formed by the image forming processor under second control of the control processor based on the data repeatedly acquired by the data acquisition unit.

* * * * *